(12) United States Patent
Zagar et al.

(10) Patent No.: US 7,674,750 B2
(45) Date of Patent: Mar. 9, 2010

(54) SYNERGISTICALLY ACTING HERBICIDAL MIXTURES

(75) Inventors: Cyrill Zagar, Mannheim (DE); Adam F. Burnhams, Cary, NC (US); Peter Dombo, Wiesbaden (DE); Andreas Landes, Roemerberg-Heiligenstein (DE); Bernd Sievernich, Hassloch (DE); Herve R. Vantieghem, Stutensee-Staffort (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 725 days.

(21) Appl. No.: 10/548,715

(22) PCT Filed: Mar. 12, 2004

(86) PCT No.: PCT/EP2004/002631

§ 371 (c)(1),
(2), (4) Date: Sep. 13, 2005

(87) PCT Pub. No.: WO2004/080173

PCT Pub. Date: Sep. 23, 2004

(65) Prior Publication Data

US 2006/0167018 A1 Jul. 27, 2006

Related U.S. Application Data

(60) Provisional application No. 60/453,974, filed on Mar. 13, 2003.

(51) Int. Cl.
*A01N 43/90* (2006.01)
*A01N 43/40* (2006.01)
*A61K 31/00* (2006.01)

(52) U.S. Cl. .................. 504/118; 504/130; 504/129; 504/214

(58) Field of Classification Search .......... 504/116, 504/118, 129, 130, 214; 514/350, 314
See application file for complete search history.

(56) References Cited

U.S. PATENT DOCUMENTS

| 6,849,578 B1 * | 2/2005 | Wellmann et al. ............ 504/130 |
| 2002/0055435 A1 * | 5/2002 | Baltruschat et al. ......... 504/103 |
| 2003/0060367 A1 | 3/2003 | Bieringer et al. |

FOREIGN PATENT DOCUMENTS

| WO | WO 94/07368 A1 | 4/1994 |
| WO | WO 01/26466 A2 | 4/2001 |
| WO | WO 0135740 A2 * | 5/2001 |
| WO | WO 03/015520 A1 | 2/2003 |

OTHER PUBLICATIONS

Anonymous, 2-(2,2-difluoroethoxy)-6-trifluoromehtyl-N-(5,8-dimethoxy[1,2,4-c]pyrimidin-2-yl)bensulfonamide and Its Use As a Herbicide in Mixtures, Oct. 2002, Research Disclosure, Research Disclosure No. 462055.*

* cited by examiner

*Primary Examiner*—Johann R Richter
*Assistant Examiner*—Andriae M Holt
(74) *Attorney, Agent, or Firm*—Rothwell, Figg, Ernst & Manbeck, P.C.

(57) ABSTRACT

A synergistic herbicidal mixture comprising A) picolinafen; or one of its environmentally compatible salts; and B) a synergistically effective amount of at least a triazolopyrimidine herbicide selected from the triazolopyrimidine sulfonanilides and penoxsulam; or one of its environmentally compatible salts or esters; and, if desired, C) at least a safener. Compositions comprising these mixtures, processes for the preparation of these compositions and their use for controlling undesired plants.

14 Claims, No Drawings

SYNERGISTICALLY ACTING HERBICIDAL MIXTURES

CROSS REFERENCE TO RELATED APPLICATION

This application is a 35 USC § 371 National Phase Entry Application from PCT/EP2004/002631, filed Mar. 17, 2004, and designating the United States, which claims the benefit of U.S. Provisional 60/453,974, filed Mar. 13, 2003.

The present invention relates to a synergistic herbicidal mixture comprising
A) picolinafen (I)

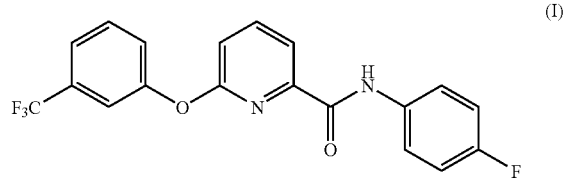

or one of its environmentally compatible salts;

and

B) a synergistically effective amount of at least a triazolopyrimidine herbicide selected from the triazolopyrimidine sulfonanilides and penoxsulam;
or one of its environmentally compatible salts or esters;

and, if desired,

C) at least a safener selected from the group of dichlormid, benoxacor, LAB 145 138, MG-191, furilazole, cyometrinil, oxabetrinil, fluxofenim, flurazole, naphthalic acid anhydride, fenclorim, fenchlorazole-ethyl, mefenpyr, isoxadifen, cloquintocet, 1-ethyl-4-hydroxy-3(1H-tetrazol-5-yl)-1H-quinolin-2-one, 4-carboxy-methyl-chroman-4-carboxylic acid, N-(2-methoxybenzyl)-4-(3-methylureido)-benzenesulfon-amide and (3-oxo-isothiochroman-4-ylidenmethoxy)acetic acid methyl ester;
or one of its environmentally compatible salts, esters or amides;

The invention furthermore relates to herbicidal compositions comprising a herbicidally active amount of a synergistic herbicidal mixture as defined above and at least one liquid and/or solid carrier and, if desired, at least one surfactant.

Moreover, the invention relates to processes for the preparation of these compositions and to a method of controlling undesirable vegetation.

WO 94/07368 and WO 01/26466 disclose mixtures of picolinafen with special further herbicides. However, in crop protection products, it is always desirable to increase the specific activity of an active ingredient and the reliability of action. It is an object of the present invention to increase the activity and/or selectivity of picolinafen against undesirable harmful plants.

We have found that this object is achieved by the mixtures defined at the outset. We have furthermore found herbicidal compositions which comprise these mixtures, processes for their preparation, and methods of controlling undesirable vegetation. In the last-mentioned cases, it is irrelevant whether the herbicidally active compounds of group A), B) and, if desired, C) are formulated and applied jointly or separately and in which sequence they are applied in the case of separate application.

The mixtures according to the invention show a synergistic effect; the compatibility of the herbicidally active compounds of group A), B) and, if desired C) for certain crop plants is generally retained.

Suitable triazolopyrimidine sulfonanilides are for example optionally substituted (1,2,4)triazolo[1,5-c]pyrimidine sulfonanilides and optionally substituted (1,2,4)triazolo-[1,5-a]pyrimidine sulfonanilides.

When any compounds are designated as being optionally substituted, the substituent groups which are optionally present may be any of those customarily employed in the modification and/or development of pesticidal compounds and are especially substituents that maintain or enhance the herbicidal activity associated with the compounds of the present invention, or influence persistence of action, soil or plant penetration, or any other desirable property of such herbicidal compounds. There may be one or more of the same or different substituents present in each part of the molecule.

Preferred are optionally substituted (1,2,4)triazolo[1,5-c] pyrimidine sulfonanilides of formula IIa,

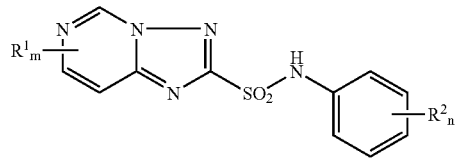

wherein
$R^1$ is halogen, $C_1$-$C_4$-alkyl, $C_1$-$C_4$-alkoxy, $C_1$-$C_4$-haloalkyl and $C_1$-$C_4$-haloalkoxy;
especially halogen, like fluorine, chlorine and bromine; $C_1$-$C_4$-alkyl, like methyl and ethyl; $C_1$-$C_4$-alkoxy, like methoxy and ethoxy;
$R^2$ is halogen, $C_1$-$C_4$-alkyl, $C_1$-$C_4$-alkoxy, $C_1$-$C_4$-haloalkyl, $C_1$-$C_4$-haloalkoxy and hydroxycarbonyl;
especially halogen, like fluorine and chlorine; $C_1$-$C_4$-alkyl, like methyl and ethyl; and hydroxycarbonyl;
m 0, 1, 2 or 3;
especially 1 or 2;
n 0, 1, 2 or 3;
especially 2;

Examples for optionally substituted (1,2,4)triazolo[1,5-c] pyrimidine sulfonanilides of formula IIa are inter alia cloransulam, diclosulam and florasulam.

Also preferred are optionally substituted (1,2,4)triazolo[1, 5-a]pyrimidine sulfonanilides of formula IIb,

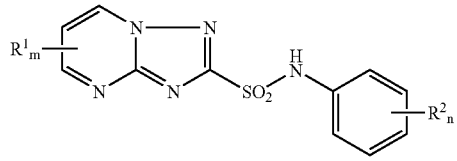

wherein
$R^1$ is halogen, $C_1$-$C_4$-alkyl, $C_1$-$C_4$-alkoxy, $C_1$-$C_4$-haloalkyl and $C_1$-$C_4$-haloalkoxy;
especially halogen, like fluorine, chlorine and bromine; $C_1$-$C_4$-alkyl, like methyl and ethyl; $C_1$-$C_4$-alkoxy, like methoxy and ethoxy;

$R^2$ is halogen, $C_1$-$C_4$-alkyl, $C_1$-$C_4$-alkoxy, $C_1$-$C_4$-haloalkyl, $C_1$-$C_4$-haloalkoxy and hydroxycarbonyl;
especially halogen, like fluorine and chlorine; and $C_1$-$C_4$-alkyl, like methyl and ethyl;

m 0, 1, 2 or 3;
especially 1 or 2;
n 0, 1, 2 or 3;
especially 2 or 3.

Examples for optionally substituted (1,2,4)triazolo[1,5-a]pyrimidine sulfonanilides of formula IIb are inter alia flumetsulam and metosulam.

The compounds of group A), B) and, if desired C) may exist, or be used, in the form of their environmentally compatible salts, esters and amides.

Suitable salts, esters and amides are, in general, those ones which do not adversely affect the herbicidal action or safening of the active ingredients.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, it being possible in this case, if desired, for one to four atoms to be replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl)-ammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of suitable acid addition salts are mainly chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and the anions of $C_1$-$C_4$-alkanoyl acids, preferably formate, acetate, propionate and butyrate.

Suitable esters are alkly-, alkoxyalkyl-, allyl-, propargyl- and oxetan-3-ylesters, preferably $C_1$-$C_{10}$-esters, for example methyl-, ethyl-, propyl-, isopropyl-, butyl-, isobutyl-, pentyl-, mexyl-(=1-methyl-hexyl) or isoctyl-(=2-ethylhexyl)ester, $C_1$-$C_4$-alkoxy-ethyl-esters, for example methoxyethyl-, ethoxyethyl- or butoxyethyl-ester, allylesters, proparyglesters and oxetan-3-ylesters.

Suitable amides are "amide" itself, alkyl- and dialkyl-amides as well as anilides, preferably $C_1$-$C_4$-alkyl-amides, for example methyl- or ethyl-amide, di($C_1$-$C_4$-alkyl)-amides, for example dimethyl- or diethyl amide, or anilides, preferably anilide itself or 2-chloro-anilide.

The compounds of components A), B) and, if desired C) as well as their salts, esters and amides, also may exist in the form of the pure enantiomere, and also as racemates or diastereomer mixtures.

Preferred synergistic mixtures according to the invention comprise as component A) picolinafen and as component B) at least a triazolopyrimidine sulfonanilide.

Especially preferred are synergistic mixtures which comprise as component A) picolinafen and as component B) at least an optionally substituted (1,2,4)triazolo-[1,5-c]pyrimidine sulfonanilide.

Particularly preferred are synergistic mixtures which comprise as component A) picolinafen and as component B) at least an optionally substituted (1,2,4)triazolo-[1,5-c]pyrimidine sulfonanilides of formula IIa.

Extraordinary preferred are synergistic mixtures which comprise as component A) picolinafen and as component B) cloransulam, especially cloransulam methyl.

Also extraordinary preferred are synergistic mixtures which comprise as component A) picolinafen and as component B) diclosulam.

Also extraordinary preferred are synergistic mixtures which comprise as component A) picolinafen and as component B) florasulam.

Also especially preferred are synergistic mixtures which comprise as component A) picolinafen and as component B) at least an optionally substituted (1,2,4)triazolo-[1,5-a]pyrimidine sulfonanilide.

Particularly preferred are synergistic mixtures which comprise as component A) picolinafen and as component B) at least an optionally substituted (1,2,4)triazolo[1,5-a]pyrimidine sulfonanilides of formula IIb.

Extraordinary preferred are synergistic mixtures which comprise as component A) picolinafen and as component B) flumetsulam.

Also extraordinary preferred are synergistic mixtures which comprise as component A) picolinafen and as component B) metosulam.

Also preferred are synergistic mixtures according to the invention which comprise as component A) picolinafen and component B) penoxulam.

Also preferred are synergistic mixtures according to the invention which comprise as component C) cloquintocet, preferably cloquintocet "acid", cloquintocet mexyl or cloquintocet mexyl×n hydrate (n=2 to 6); isoxadifen, preferably isoxadifen "acid" or isoxadifen ethyl; or mefenpyr, preferably mefenpyr "acid" or mefenpyr diethyl.

Especially preferred are synergistic mixtures which comprise as component C) cloquintocet, preferably cloquintocet "acid", cloquintocet mexyl or cloquintocet mexyl×n hydrate (n=2 to 6).

Particularly preferred are synergistic mixtures which comprise as component A) picolinafen, as component B) at least a triazolopyrimidine sulfonanilide and as component C) cloquintocet, preferably cloquintocet "acid", cloquintocet mexyl or cloquintocet mexyl×n hydrate (n=2 to 6).

Extraordinary preferred are synergistic mixtures which comprise as component A) picolinafen, as component B) at least an optionally substituted (1,2,4)-triazolo[1,5-c]pyrimidine sulfonanilide and component C) cloquintocet, preferably cloquintocet "acid", cloquintocet mexyl or cloquintocet mexyl×n hydrate (n=2 to 6).

Especially extraordinary preferred are synergistic mixtures which comprise as component A) picolinafen, as component B) at least an optionally substituted (1,2,4)triazolo[1,5-c]pyrimidine sulfonanilides of formula IIa and as component C) cloquintocet, preferably cloquintocet "acid", cloquintocet mexyl or cloquintocet mexyl×n hydrate (n=2 to 6).

Particularly extraordinary preferred are synergistic mixtures which comprise as component A) picolinafen, as component B) cloransulam, especially cloransulam methyl, and as component C) cloquintocet, preferably cloquintocet "acid", cloquintocet mexyl or cloquintocet mexyl×n hydrate (n=2 to 6).

Also particularly extraordinary preferred are synergistic mixtures which comprise as component A) picolinafen, as component B) diclosulam and as component C) cloquintocet, preferably cloquintocet "acid", cloquintocet mexyl or cloquintocet mexyl×n hydrate (n=2 to 6).

Also particularly extraordinary preferred are synergistic mixtures which comprise as component A) picolinafen, as component B) and florasulam and as component C) cloquintocet, preferably cloquintocet "acid", cloquintocet mexyl or cloquintocet mexyl×n hydrate (n=2 to 6).

Also extraordinary preferred are synergistic mixtures which comprise as component A) picolinafen, as component B) at least an optionally substituted (1,2,4)-triazolo[1,5-a]pyrimidine sulfonanilide and as component C) cloquintocet, preferably cloquintocet "acid", cloquintocet mexyl or cloquintocet mexyl×n hydrate (n=2 to 6).

Especially extraordinary preferred are synergistic mixtures which comprise as component A) picolinafen and as component B) at least an optionally substituted (1,2,4)triazolo[1,5-a]pyrimidine sulfonanilides of formula IIb and as component C) cloquintocet, preferably cloquintocet "acid", cloquintocet mexyl or cloquintocet mexyl×n hydrate (n=2 to 6).

Particularly extraordinary preferred are synergistic mixtures which comprise as component A) picolinafen, as component B) flumetsulam and as component C) cloquintocet, preferably cloquintocet "acid", cloquintocet mexyl or cloquintocet mexyl×n hydrate (n=2 to 6).

Also particularly extraordinary preferred are synergistic mixtures which comprise as component A) picolinafen, as component B) metosulam and as component C) cloquintocet, preferably cloquintocet "acid", cloquintocet mexyl or cloquintocet mexyl×n hydrate (n=2 to 6).

Also particularly preferred are synergistic mixtures which comprise as component A) picolinafen, as component B) penoxulam and as component C) cloquintocet, preferably cloquinto-cet "acid", cloquintocet mexyl or cloquintocet mexyl×n hydrate (n=2 to 6).

Especially preferred are synergistic mixtures which comprise as component C) isoxadifen, preferably isoxadifen "acid" or isoxadifen ethyl.

Particularly preferred are synergistic mixtures which comprise as component A) picolinafen, as component B) at least a triazolopyrimidine sulfonanilide and as component C) isoxadifen, preferably isoxadifen "acid" or isoxadifen ethyl.

Extraordinary preferred are synergistic mixtures which comprise as component A) picolinafen, as component B) at least an optionally substituted (1,2,4)triazolo[1,5-c]pyrimidine sulfonanilide and as component C) isoxadifen, preferably isoxadifen "acid" or isoxadifen ethyl.

Especially extraordinary preferred are synergistic mixtures which comprise as component A) picolinafen, as component B) at least an optionally substituted (1,2,4)triazolo[1,5-c]pyrimidine sulfonanilides of formula IIa and as component C) isoxadifen, preferably isoxadifen "acid" or isoxadifen ethyl.

Particularly extraordinary preferred are synergistic mixtures which comprise as component A) picolinafen, as component B) cloransulam, especially cloransulam methyl, and as component C) isoxadifen, preferably isoxadifen "acid" or isoxadifen ethyl.

Also particularly extraordinary preferred are synergistic mixtures which comprise as component A) picolinafen, as component B) diclosulam and as component C) isoxadifen, preferably isoxadifen "acid" or isoxadifen ethyl.

Also particularly extraordinary preferred are synergistic mixtures which comprise as component A) picolinafen, as component B) florasulam and as component C) isoxadifen, preferably isoxadifen "acid" or isoxadifen ethyl.

Also extraordinary preferred are synergistic mixtures which comprise as component A) picolinafen, as component B) at least an optionally substituted (1,2,4)-triazolo[1,5-a]pyrimidine sulfonanilide and as component C) isoxadifen, preferably isoxadifen "acid" or isoxadifen ethyl.

Especially extraordinary preferred are synergistic mixtures which comprise as component A) picolinafen, as component B) at least an optionally substituted (1,2,4)triazolo[1,5-a]pyrimidine sulfonanilide of formula IIb and as component C) isoxadifen, preferably isoxadifen "acid" or isoxadifen ethyl.

Particularly extraordinary preferred are synergistic mixtures which comprise as component A) picolinafen, as component B) flumetsulam and as component C) isoxadifen, preferably isoxadifen "acid" or isoxadifen ethyl.

Also particularly extraordinary preferred are synergistic mixtures which comprise as component A) picolinaen, as component B) metosulam and as component C) isoxadifen, preferably isoxadifen "acid" or isoxadifen ethyl.

Also particularly preferred are synergistic mixtures which comprise as component A) picolinafen, as component B) penoxulam and as component C) isoxadifen, preferably isoxadifen "acid" or isoxadifen ethyl.

Especially preferred are synergistic mixtures which comprise as compound of group C) mefenpyr, preferably mefenpyr "acid" or mefenpyr diethyl.

Particularly preferred are synergistic mixtures which comprise as component A) picolinafen, as component B) at least a triazolopyrimidine sulfonanilide and as component C) mefenpyr, preferably mefenpyr "acid" or mefenpyr diethyl.

Extraordinary preferred are synergistic mixtures which comprise as component A) picolinafen, as component B) at least an optionally substituted (1,2,4)triazolo[1,5-c]pyrimidine sulfonanilide and as component C) mefenpyr, preferably mefenpyr "acid" or mefenpyr diethyl.

Especially extraordinary preferred are synergistic mixtures which comprise as component A) picolinafen, as component B) at least an optionally substituted (1,2,4)triazolo[1,5-c]pyrimidine sulfonanilide of formula IIa and as component C) mefenpyr, preferably mefenpyr "acid" or mefenpyr diethyl.

Particularly extraordinary preferred are synergistic mixtures which comprise as component A) picolinafen, as component B) cloransulam, especially cloransulam methyl, and as component C) mefenpyr, preferably mefenpyr "acid" or mefenpyr diethyl.

Also particularly extraordinary preferred are synergistic mixtures which comprise as component A) picolinafen, as component B) diclosulam and as component C) mefenpyr, preferably mefenpyr "acid" or mefenpyr diethyl.

Also particularly extraordinary preferred are synergistic mixtures which comprise as component A) picolinafen, as component B) florasulam and as component C) mefenpyr, preferably mefenpyr "acid" or mefenpyr diethyl.

Also extraordinary preferred are synergistic mixtures which comprise as component A) picolinafen, as component B) at least an optionally substituted (1,2,4)triazolo[1,5-a]pyrimidine sulfonanilide and as component C) mefenpyr, preferably mefenpyr "acid" or mefenpyr diethyl.

Especially extraordinary preferred are synergistic mixtures which comprise as component A) picolinafen and as component B) at least an optionally substituted (1,2,4)triazolo[1,5-a]pyrimidine sulfonanilide of formula IIb and as component C) mefenpyr, preferably mefenpyr "acid" or mefenpyr diethyl.

Particularly extraordinary preferred are synergistic mixtures which comprise as component A) picolinafen, as component B) flumetsulam and as component C) mefenpyr, preferably mefenpyr "acid" or mefenpyr diethyl.

Also particularly extraordinary preferred are synergistic mixtures which comprise as component A) picolinafen, as component B) metosulam and as component C) mefenpyr, preferably mefenpyr "acid" or mefenpyr diethyl.

Also particularly preferred are synergistic mixtures which comprise as component A) picolinafen, as component B) penoxsulam and as component C) mefenpyr, preferably mefenpyr "acid" or mefenpyr diethyl.

Moreover it may be advantageous that the synergistic mixture according to the present invention comprises as active ingredients a compound of group A), at least a compound of group B), if desired at least a compound of group C), and furthermore at least a herbicide of group D).

Examples of suitable herbicides of group D) are, inter alia, acetyl-CoA carboxylase inhibitors (ACC), acetolactate synthase inhibitors (ALS), amides, auxin herbicides, auxin transport inhibitors, carotenoid biosynthesis inhibitors, enolpyruvylshikimate 3-phosphate synthase inhibitors (EPSPS), glutamine synthetase inhibitors, lipid biosynthesis inhibitors, mitosis inhibitors, protoporphyrinogen IX oxidase inhibitors, photosynthesis inhibitors, synergists, growth substances, cell wall biosynthesis inhibitors and a variety of other herbicides.

Special examples of herbicides of group D) which can be used, are inter alia,

D1 acetyl-CoA carboxylase inhibitors (ACC), for example
cyclohexenone oxime ethers, such as alloxydim, clethodim, cloproxydim, cycloxydim, sethoxydim, tralkoxydim, butroxydim, clefoxydim or tepraloxydim;
phenoxyphenoxypropionic esters, such as clodinafop-propargyl, cyhalofop-butyl, diclofop-methyl, fenoxaprop-ethyl, fenoxaprop-P-ethyl, fenthiaprop-ethyl, fluazifop-butyl, fluazifop-P-butyl, haloxyfop-ethoxyethyl, haloxyfop-methyl, haloxyfop-P-methyl, isoxapyrifop, propaquizafop, quizalofop-ethyl, quizalofop-P-ethyl or quizalofop-tefuryl; or
arylaminopropionic acids, such as flamprop-methyl or flamprop-isopropyl;

D2 acetolactate synthase inhibitors (ALS), for example
imidazolinones, such as imazapyr, imazaquin, imazamethabenz-methyl (imazame), imazamox, imazapic or imazethapyr;
pyrimidyl ethers, such as pyrithiobac-acid, pyrithiobac-sodium, bispyribac-sodium, KIH-6127 or pyribenzoxym;
sulfonylureas, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide;

D3 amides, for example
allidochlor (CDAA), benzoylprop-ethyl, bromobutide, chlorthiamid, diphenamid, etobenzanid (benzchlomet), fluthiamide, fosamin or monalide;

D4 auxin herbicides, for example
pyridinecarboxylic acids, such as clopyralid or picloram; or
2,4-D or benazolin;

D5 auxin transport inhibitors, for example
naptalame or diflufenzopyr;

D6 carotenoid biosynthesis inhibitors, for example
benzofenap, clomazone (dimethazone), diflufenican, fluorochloridone, fluridone, pyrazolynate, pyrazoxyfen, isoxaflutole, isoxachlortole, mesotrione, sulcotrione (chlormesulone), ketospiradox, flurtamone, norflurazon or amitrol;

D7 enolpyruvylshikimate-3-phosphate synthase inhibitors (EPSPS), for example
glyphosate or sulfosate;

D8 glutamine synthetase inhibitors, for example
bilanafos (bialaphos) or glufosinate-ammonium;

D9 lipid biosynthesis inhibitors, for example
anilides, such as anilofos or mefenacet;
chloroacetanilides, such as dimethenamid, S-dimethenamid, acetochlor, alachlor, butachlor, butenachlor, diethatyl-ethyl, dimethachlor, metazachlor, metolachlor, S-metolachlor, pretilachlor, propachlor, prynachlor, terbuchlor, thenylchlor or xylachlor;
thioureas, such as butylate, cycloate, di-allate, dimepiperate, EPTC, esprocarb, molinate, pebulate, prosulfocarb, thiobencarb (benthiocarb), tri-allate or vernolate; or
benfuresate or perfluidone;

D10 mitosis inhibitors, for example
carbamates, such as asulam, carbetamid, chlorpropham, orbencarb, pronamid (propyzamid), propham or tiocarbazil;
dinitroanilines, such as benefin, butralin, dinitramin, ethalfluralin, fluchloralin, oryzalin, pendimethalin, prodiamine or trifluralin;
pyridines, such as dithiopyr or thiazopyr; or butamifos, chlorthal-dimethyl (DCPA) or maleic hydrazide;

D11 protoporphyrinogen IX oxidase inhibitors, for example
diphenyl ethers, such as acifluorfen, acifluorfen-sodium, aclonifen, bifenox, chlomitrofen (CNP), ethoxyfen, fluorodifen, fluoroglycofen-ethyl, fomesafen, furyloxyfen, lactofen, nitrofen, nitrofluorfen or oxyfluorfen;
oxadiazoles, such as oxadiargyl or oxadiazon;
cyclic imides, such as azafenidin, butafenacil, carfentrazone-ethyl, cinidon-ethyl, flumiclorac-pentyl, flumioxazin, flumipropyn, flupropacil, fluthiacet-methyl, sulfentrazone or thidiazimin; or
pyrazoles, such as ET-751, JV 485 or nipyraclofen;

D12 photosynthesis inhibitors, for example
propanil, pyridate or pyridafol;
benzothiadiazinones, such as bentazone;
dinitrophenols, for example bromofenoxim, dinoseb, dinoseb-acetate, dinoterb or DNOC;
dipyridylenes, such as cyperquat-chloride, difenzoquat-methylsulfate, diquat or paraquat-dichloride;
ureas, such as chlorbromuron, chlorotoluron, difenoxuron, dimefuron, diuron, ethidimuron, fenuron, fluometuron, isoproturon, isouron, linuron, methabenzthiazuron, methazole, metobenzuron, metoxuron, monolinuron, neburon, siduron or tebuthiuron;
phenols, such as bromoxynil or ioxynil;
chloridazon;
triazines, such as ametryn, atrazine, cyanazine, desmetryn, dimethamethryn, hexazinone, prometon, prometryn, propazine, simazine, simetryn, terbumeton, terbutryn, terbutylazine or trietazine;
triazinones, such as metamitron or metribuzin;
uracils, such as bromacil, lenacil or terbacil; or
biscarbamates, such as desmedipham or phenmedipham;

D13 synergists, for example
oxiranes, such as tridiphane;

D14 growth substances, for example
aryloxyalkanoic acids, such as 2,4-DB, clomeprop, dichlorprop, dichlorprop-P (2,4-DP-P), fluoroxypyr, MCPA, MCPB, mecoprop, mecoprop-P or triclopyr;
benzoic acids, such as chloramben or dicamba; or
quinolinecarboxylic acids, such as quinclorac or quinmerac;

D15 cell wall synthesis inhibitors, for example
isoxaben or dichlobenil;

D16 various other herbicides, for example
dichloropropionic acids, such as dalapon;
dihydrobenzofurans, such as ethofumesate;
phenylacetic acids, such as chlorfenac (fenac); or
aziprotryn, barban, bensulide, benzthiazuron, benzofluor, buminafos, buthidazole, buturon, cafenstrole, chlorbufam, chlorfenprop-methyl, chloroxuron, cinmethylin, cumyluron, cycluron, cyprazine, cyprazole, dibenzyluron, dipropetryn, dymron, eglinazin-ethyl, endothall, ethiozin, flucabazone, fluorbentranil, flupoxam, isocarbamid, isopropalin, karbutilate, mefluidide, monuron, napropamide, napropanilide, nitralin, oxaciclomefone, phenisopham, piperophos, procyazine, profluralin, pyributicarb, secbumeton, sulfallate (CDEC), terbucarb, triaziflam, triazofenamid or trimeturon;

or their environmentally compatible salts, "acids", esters and amides.

Suitable salts, esters and amides are similar to those mentioned for the compounds of the group of groups A), B) and C).

The compounds of group D) as well as their salts, "acids", esters and amides, may also exist in the form of the pure enantiomere, and also as racemates or diastereomer mixtures.

Preferred are synergistic mixtures which comprise as component A) picolinafen, as component B) at least a triazolopyrimidine and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]carbonyl]-2-(trifluoromethyl)-benzenesulfon-amide.

Especially preferred are synergistic mixtures which comprise as component A) picolinafen, as component B) at least an optionally substituted (1,2,4)triazolo-[1,5-c]-pyrimidine sulfonanilide and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]-carbonyl]-2-(trifluoromethyl)-benzene-sulfonamide; especially N-[[[4-methoxy-6-(trifluoromethyl)-1,3,5-triazin-2-yl]amino]-carbonyl]-2-(trifluoromethyl)-benzenesulfon-amide.

Particularly preferred are synergistic mixtures which comprise as component A) picolinafen, as component B) at least an optionally substituted (1,2,4)triazolo-[1,5-c]pyrimidine sulfonanilides of formula IIa and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzene-sulfon-amide; especially N-[[[4-methoxy-6-(trifluoromethyl)-1,3,5-triazin-2-yl]amino]-carbonyl]-2-(trifluoromethyl)-benzenesulfon-amide.

Extraordinary preferred are synergistic mixtures which comprise as component A) picolinafen, as component B) cloransulam, especially cloransulam methyl, and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzene-sulfon-amide; especially N-[[[4-methoxy-6-(trifluoromethyl)-1,3,5-triazin-2-yl]amino]carbonyl]-2-(trifluoromethyl)-benzenesulfon-amide.

Also extraordinary preferred are synergistic mixtures which comprise as component A) picolinafen, as component B) diclosulam and as component D) at least a sulfonyl-urea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]carbonyl]-2-(trifluoromethyl)-benzenesulfon-amide.

Also extraordinary preferred are synergistic mixtures which comprise as component A) picolinafen, as component B) florasulam and as compound D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]carbonyl]-2-(trifluoromethyl)-benzenesulfon-amide.

Also especially preferred are synergistic mixtures which comprise as component A) picolinafen, as component B) at least an optionally substituted (1,2,4)triazolo[1,5-a]-pyrimidine sulfonanilide and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]carbonyl]-2-(trifluoromethyl)-benzenesulfon-amide.

Particularly preferred are synergistic mixtures which comprise as component A) picolinafen, as component B) at least an optionally substituted (1,2,4)triazolo-[1,5-a]pyrimidine sulfonanilides of formula IIb and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]carbonyl]-2-(trifluoromethyl)-benzenesulfon-amide.

Extraordinary preferred are synergistic mixtures which comprise as component A) picolinafen, as component B) flumetsulam, and as compound D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]carbonyl]-2-(trifluoromethyl)-benzenesulfon-amide.

Also extraordinary preferred are synergistic mixtures which comprise as component A) picolinafen, as component B) metosulam and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]carbonyl]-2-(trifluoromethyl)-benzenesulfon-amide.

Also preferred are synergistic mixtures which comprise as component A) picolinafen, as component B) penoxulam and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]carbonyl]-2-(trifluoromethyl)-benzenesulfon-amide.

Also preferred are synergistic mixtures according to the invention which comprise as component C) cloquintocet, preferably cloquintocet "acid", cloquintocet mexyl or cloquintocet mexyl×n hydrate (n=2 to 6); isoxadifen, preferably isoxadifen "acid" or isoxadifen ethyl; or mefenpyr, preferably mefenpyr "acid" or mefenpyr diethyl, and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]carbonyl]-2-(trifluoromethyl)-benzenesulfon-amide.

Especially preferred are synergistic mixtures which comprise as component C) cloquintocet, preferably cloquintocet "acid", cloquintocet mexyl or cloquintocet mexyl×n hydrate (n=2 to 6), and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]carbonyl]-2-(trifluoromethyl)-benzenesulfon-amide.

Particularly preferred are synergistic mixtures which comprise as component A) picolinafen, as component B) at least a triazolopyrimidine sulfonanilide, as component C) cloquintocet, preferably cloquintocet "acid", cloquintocet mexyl or cloquintocet mexyl×n hydrate (n=2 to 6), and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]carbonyl]-2-(trifluoromethyl)-benzenesulfon-amide.

Extraordinary preferred are synergistic mixtures which comprise as component A) picolinafen, as component B) at least an optionally substituted (1,2,4)triazolo-[1,5-c]-pyrimidine sulfonanilide, as component C) cloquintocet, preferably cloquintocet "acid", cloquintocet mexyl or cloquintocet mexyl×n hydrate (n=2 to 6), and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]-carbonyl]-2-(trifluoromethyl)-benzenesulfon-amide.

Especially extraordinary preferred are synergistic mixtures which comprise as component A) picolinafen, as component B) at least an optionally substituted (1,2,4)triazolo[1,5-c]pyrimidine sulfonanilide of formula IIa, as component C) cloquintocet, preferably cloquintocet "acid", cloquintocet mexyl or cloquintocet mexyl×n hydrate (n=2 to 6), and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]carbonyl]-2-(trifluoromethyl)-benzenesulfon-amide.

Particularly extraordinary preferred are synergistic mixtures which comprise as component A) picolinafen, as component B) cloransulam, especially cloransulam methyl, as component C) cloquintocet, preferably cloquintocet "acid", cloquintocet mexyl or cloquintocet mexyl×n hydrate (n=2 to 6), and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]-amino]carbonyl]-2-(trifluoromethyl)-benzenesulfon-amide; especially N-[[[4-methoxy-6-(trifluoromethyl)-1,3,5-triazin-2-yl]amino]carbonyl]-2-(trifluoromethyl)-benzenesulfon-amide.

Also particularly extraordinary preferred are synergistic mixtures which comprise as component A) picolinafen, as component B) diclosulam, as component C) cloquintocet, preferably cloquintocet "acid", cloquintocet mexyl or cloquintocet mexyl×n hydrate (n=2 to 6), and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]-amino]carbonyl]-2-(trifluoromethyl)-benzenesulfon-amide.

Also particularly extraordinary preferred are synergistic mixtures which comprise as component A) picolinafen, as component B) florasulam, as component C) cloquintocet, preferably cloquintocet "acid", cloquintocet mexyl or cloquintocet mexyl×n hydrate (n=2 to 6), and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]carbonyl]-2-(trifluoromethyl)-benzenesulfon-amide.

Also extraordinary preferred are synergistic mixtures which comprise as component A) picolinafen, as component B) at least an optionally substituted (1,2,4)-triazolo-[1,5-a]pyrimidine sulfonanilide, as component C) cloquintocet, preferably cloquintocet "acid", cloquintocet mexyl or cloquintocet mexyl×n hydrate (n=2 to 6), and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]-carbonyl]-2-(trifluoromethyl)-benzenesulfon-amide.

Especially exraordinary preferred are synergistic mixtures which comprise as component A) picolinafen, as component B) at least an optionally substituted (1,2,4)triazolo[1,5-a]pyrimidine sulfonanilide of formula IIb, as component C) cloquintocet, preferably cloquintocet "acid", cloquintocet mexyl or cloquintocet mexyl×n hydrate (n=2 to 6), and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]carbonyl]-2-(trifluoromethyl)-benzenesulfon-amide.

Particularly extraordinary preferred are synergistic mixtures which comprise as component A) picolinafen, as component B) flumetsulam, as component C) cloquintocet, preferably cloquintocet "acid", cloquintocet mexyl or cloquintocet mexyl×n hydrate (n=2 to 6), and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]-amino]carbonyl]-2-(trifluoromethyl)-benzenesulfon-amide; especially N-[[[4-methoxy-6-(trifluoromethyl)-1,3,5-triazin-2-yl]amino]carbonyl]-2-(trifluoromethyl)-benzenesulfon-amide.

Also particularly extraordinary preferred are synergistic mixtures which comprise as component A) picolinafen, as component B) metosulam, as component C) cloquintocet, preferably cloquintocet "acid", cloquintocet mexyl or cloquintocet mexyl×n hydrate (n=2 to 6), and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]-amino]carbonyl]-2-(trifluoromethyl)-benzenesulfon-amide.

Also particularly preferred are synergistic mixtures which comprise as component A) picolinafen, as component B) penoxulam, as component C) cloquintocet, preferably cloquintocet "acid", cloquintocet mexyl or cloquintocet mexyl×n hydrate (n=2 to 6), and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetan-yl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]-amino]carbonyl]-2-(trifluoromethyl)-benzenesulfon-amide; especially N-[[[4-methoxy-6-(trifluoromethyl)-1,3,5-triazin-2-yl]amino]carbonyl]-2-(trifluoromethyl)-benzenesulfon-amide.

Especially preferred are synergistic mixtures which comprise as component C) isoxadifen, preferably isoxadifen "acid" or isoxadifen ethyl, and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]carbonyl]-2-(trifluoromethyl)-benzenesulfon-amide.

Particularly preferred are synergistic mixtures which comprise as component A) picolinafen, as component B) at least a triazolopyrimidine sulfonanilide, as component C) isoxadifen, preferably isoxadifen "acid" or isoxadifen ethyl, and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]carbonyl]-2-(trifluoromethyl)-benzenesulfon-amide.

Extraordinary preferred are synergistic mixtures which comprise as component A) picolinafen, as component B) at least an optionally substituted (1,2,4)triazolo[1,5-c]pyrimidine sulfonanilide, as component C) isoxadifen, preferably isoxadifen "acid" or isoxadifen ethyl, and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]carbonyl]-2-(trifluoromethyl)-benzenesulfon-amide.

Especially extraordinary preferred are synergistic mixtures which comprise as component A) picolinafen, as component B) at least an optionally substituted (1,2,4)triazolo[1,5-c]pyrimidine sulfonanilide of formula IIa, as component C) isoxadifen, preferably isoxadifen "acid" or isoxadifen ethyl, and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]-amino]carbonyl]-2-(trifluoromethyl)-benzenesulfonamide; especially N-[[[4-methoxy-6-(trifluoromethyl)-1,3,5-triazin-2-yl]amino]-carbonyl]-2-(trifluoromethyl)-benzenesulfonamide.

Particularly extraordinary preferred are synergistic mixtures which comprise as component A) picolinafen, as component B) cloransulam, especially cloransulam methyl, as component C) isoxadifen, preferably isoxadifen "acid" or isoxadifen ethyl, and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]-amino]carbonyl]-2-(trifluoromethyl)-benzenesulfonamide; especially N-[[[4-methoxy-6-(trifluoromethyl)-1,3,5-triazin-2-yl]amino]carbonyl]-2-(trifluoromethyl)-benzenesulfonamide.

Also particularly extraordinary preferred are synergistic mixtures which comprise as component A) picolinafen, as component B) diclosulam, as component C) isoxadifen, preferably isoxadifen "acid" or isoxadifen ethyl, and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-y]amino]carbonyl]-2-(trifluoromethyl)-benzenesulf-amide; especially N-[[[4-methoxy-6-(tri-fluoromethyl)-1,3,5-triazin-2-yl]amino]-carbonyl]-2-(trifluoromethyl)-benzenesulf-amide.

Also particularly extraordinary preferred are synergistic mixtures which comprise as component A) picolinafen, as component B) florasulam, as component C) isoxadifen, preferably isoxadifen "acid" or isoxadifen ethyl, and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]carbonyl]-2-(trifluoromethyl)-benzenesulfon-amide.

Also extraordinary preferred are synergistic mixtures which comprise as component A) picolinafen, as component B) at least an optionally substituted (1,2,4)triazolo-[1,5-a]pyrimidine sulfonanilide, as component C) isoxadifen, preferably isoxadifen "acid" or isoxadifen ethyl, and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]carbonyl]-2-(trifluoromethyl)-benzenesulfon-amide.

Especially extraordinary preferred are synergistic mixtures which comprise as component A) picolinafen and as component B) at least an optionally substituted (1,2,4)triazolo[1,5-a]pyrimidine sulfonanilide of formula IIb, as component C) isoxadifen, preferably isoxadifen "acid" or isoxadifen ethyl, and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl; prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino] carbonyl]-2-(trifluoromethyl)-benzenesulfonamide; especially N-[[[4-methoxy-6-(trifluoromethyl)-1,3,5-triazin-2-yl]amino]-carbonyl]-2-(trifluoromethyl)-benzenesulfonamide.

Particularly extraordinary preferred are synergistic mixtures which comprise as component A) picolinafen, as component B) flumetsulam, as component C) isoxadifen, preferably isoxadifen "acid" or isoxadifen ethyl, and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron; thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]-carbonyl]-2-(trifluoromethyl)-benzenesulfon-amide.

Also particularly extraordinary preferred are synergistic mixtures which comprise as component A) picolinafen, as component B) metosulam, as component C) isoxadifen, preferably isoxadifen "acid" or isoxadifen ethyl, and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]-carbonyl]-2-(trifluoromethyl)-benzenesulfon-amide.

Also particularly preferred are synergistic mixtures which comprise as component A) picolinafen, as component B) penoxulam, as component C) isoxadifen, preferably isoxadifen "acid" or isoxadifen ethyl, and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino] carbonyl]-2-(trifluoromethyl)-benzenesulfon-amide.

Especially preferred are synergistic mixtures which comprise as component C) mefenpyr, preferably mefenpyr "acid" or mefenpyr diethyl, and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]-carbonyl]-2-(trifluoromethyl)-benzenesulfon-amide; especially N-[[[4-methoxy-6-(trifluoromethyl)-1,3,5-triazin-2-yl]amino]carbonyl]-2-(trifluoromethyl)-benzenesulfon-amide.

Particularly preferred are synergistic mixtures which comprise as component A) picolinafen, as component B) at least a triazolopyrimidine sulfonanilide, as component C) mefenpyr, preferably mefenpyr "acid" or mefenpyr diethyl, and component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino] carbonyl]-2-(trifluoromethyl)-benzenesulfon-amide.

Extraordinary preferred are synergistic mixtures which comprise as component A) picolinafen, as component B) at least an optionally substituted (1,2,4)triazolo-[1,5-c]pyrimidine sulfonanilide, as component C) mefenpyr, preferably mefenpyr "acid" or mefenpyr diethyl, and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoro-methyl)-benzenesulfon-amide; especially N-[[[4-methoxy-6-(trifluoromethyl)-1,3,5-triazin-2-yl]amino] carbonyl]-2-(trifluoromethyl)-benzenesulfon-amide.

Especially extraordinary preferred are synergistic mixtures which comprise as component A) picolinafen, as component B) at least an optionally substituted (1,2,4)triazolo[1,5-c]pyrimidine sulfonanilide of formula IIa, as component C) mefenpyr, preferably mefenpyr "acid" or mefenpyr diethyl, and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino] carbonyl]-2-(trifluoromethyl)-benzenesulfon-amide; especially N-[[[4-methoxy-6-(trifluoromethyl)-1,3,5-triazin-2-yl]amino]-carbonyl]-2-(trifluoromethyl)-benzenesulfon-amide.

Particularly extraordinary preferred are synergistic mixtures which comprise as component A) picolinafen, as component B) cloransulam, especially cloransulam methyl, as component C) mefenpyr, preferably mefenpyr "acid" or mefenpyr diethyl, and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino] carbonyl]-2-(trifluoromethyl)-benzenesulfon-amide; especially N-[[[4-methoxy-6-(trifluoromethyl)-1,3,5-triazin-2-yl]amino] carbonyl]-2-(trifluoromethyl)-benzenesulfon-amide.

Also particularly extraordinary preferred are synergistic mixtures which comprise as component A) picolinafen, as component B) diclosulam, as component C) mefenpyr, preferably mefenpyr "acid" or mefenpyr diethyl, and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]-carbonyl]-2-(trifluoromethyl)-benzenesulfon-amide.

Also particularly extraordinary preferred are synergistic mixtures which comprise as component A) picolinafen, as component B) florasulam, as component C) mefenpyr, preferably mefenpyr "acid" or mefenpyr diethyl, and as compound D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(tri-fluoromethyl)-1,3,5-triazin-2-yl] amino]-carbonyl]-2-(trifluoromethyl)-benzenesulfon-amide.

Also extraordinary preferred are synergistic mixtures which comprise as component A) picolinafen, as component B) at least an optionally substituted (1,2,4)triazolo-[1,5-a]pyrimidine sulfonanilide, as component C) mefenpyr, preferably mefenpyr "acid" or mefenpyr diethyl, and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]-carbonyl]-2-(trifluoro-methyl)-benzenesulfon-amide; especially N-[[[4-methoxy-6-(trifluoromethyl)-1,3,5-triazin-2-yl]amino] carbonyl]-2-(trifluoromethyl)-benzenesulfon-amide.

Especially extraordinary preferred are synergistic mixtures which comprise as component A) picolinafen, as component B) at least an optionally substituted (1,2,4)triazolo[1,5-a]pyrimidine sulfonanilide of formula IIb, as component C) mefenpyr, preferably mefenpyr "acid" or mefenpyr diethyl, and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]-amino]carbonyl]-2-(trifluoromethyl)-benzenesulfon-amide; especially N-[[[4-methoxy-6-(trifluoromethyl)-1,3,5-triazin-2-yl]amino]carbonyl]-2-(trifluoromethyl)-benzenesulfon-amide.

Particularly extraordinary preferred are synergistic mixtures which comprise as component A) picolinafen, as component B) flumetsulam, as component C) mefenpyr, preferably mefenpyr "acid" or mefenpyr diethyl, and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]-carbonyl]-2-(trifluoromethyl)-benzenesulfon-amide.

Also particularly extraordinary preferred are synergistic mixtures which comprise as component A) picolinafen, as component B) metosulam, as component C) mefenpyr, preferably mefenpyr "acid" or mefenpyr diethyl, and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]-carbonyl]-2-(trifluoromethyl)-benzenesulfon-amide.

Also particularly preferred are synergistic mixtures which comprise as component A) picolinafen, as component B) penoxulam, as component C) mefenpyr, preferably mefenpyr "acid" or mefenpyr diethyl, and as component D) at least a sulfonylurea, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucarbazone, flupyrsulfuron, foramsulfuron, halosulfuron-methyl, imazosulfuron, iodosulfuron, mesosulfuron, metsulfuron-methyl, nicosulfuron, primisulfuron-methyl, prosulfuron, procarbazone, pyrazosulfuron-ethyl, rimsulfuron, sulfometuron-methyl or -3-oxetanyl, sulfosulfuron, thifensulfuron-methyl, triasulfuron, tribenuron-methyl, triflusulfuron-methyl, trifloxysulfuron or N-[[[4-methoxy-6-(trifluoromethyl)-1,3,5-triazin-2-yl]amino]carbonyl]-2-(trifluoromethyl)-benzenesulfon-amide; especially N-[[[4-methoxy-6-(trifluoromethyl)-1,3,5-triazin-2-yl]amino]carbonyl]-2-(trifluoromethyl)-benzenesulfon-amide.

Also preferred are synergistic mixtures which comprise as component A) picolinafen, as component B) at least a triazolopyrimidine and as component D) at least a compound selected from the groupd D1, D3 to D16 as well as from the imidazolinones and the pyrimidyl ethers (as defined above).

Also preferred are synergistic mixtures which comprise as component A) picolinafen, as component B) at least a triazolopyrimidine, as component C) cloquintocet, preferably cloquintocet "acid", cloquintocet mexyl or cloquintocet mexyl×n hydrate (n=2 to 6), isoxadifen, preferably isoxadifen "acid" or isoxadifen ethyl, or mefenpyr, preferably mefenpyr "acid" or mefenpyr diethyl, and as component D) at least a compound selected from the groupd D1, D3 to D16 as well as from the imidazolinones and the pyrimidyl ethers (as defined above).

Preferred are synergistic mixtures which comprise as active ingredients only picolinafen and one compound of group B).

Especially preferred synergistic mixtures thereof are in analogy to the above-mentioned ones.

Also preferred are synergistic mixtures which comprise as active ingredients only picolinafen, one compound of group B) and one compound of group C).

Especially preferred synergistic mixtures thereof are in analogy to the above-mentioned ones.

Also preferred are synergistic mixtures which comprise as active ingredients only picolinafen, one compound of group B) and one compound of group D).

Especially preferred synergistic mixtures thereof are in analogy to the above-mentioned ones.

Also preferred are synergistic mixtures which comprise as active ingredients only picolinafen, one compound of group B), one compound of group C) and one compound of group D).

Especially preferred synergistic mixtures thereof are in analogy to the above-mentioned ones.

Picolinafen is disclosed in EP 447 004.

The compounds of group B are described, for example, in U.S. Pat. No. 4,818,273 and in U.S. Pat. No. 5,163,995, especially in "The Pesticide Manual", 12$^{th}$ edition ("cloransulam" p. 196, "diclosulam" p. 283, "florasulam" p. 420, "flumetsulam" p. 438, "metosulam" p. 640); "penoxsulam" is disclosed in U.S. Pat. No. 5,858,924.

The compounds of group C) are described, for example, in

"Herbizide [Herbicides]", Hock, Fedtke, Schmidt, 1st edition, Thieme 1995 ("dichlormid" p. 263, "benoxacor" p. 263, "LAB-145138" p. 263, "MG-191" p. 263, "MON-13900" p. 263, "cyometrinil" p. 265, "oxabetrinil" p. 265, "yluxofenim" p. 265, "flurazole" p. 265, "naphtalic acid anhydride" p. 265, "fenchlorim" p. 266, "fenchlorazol" p. 266, "cloquintocet" p. 266);

WO 91/07874 ("mefenpyr");

WO 99/00020 ("1-ethyl-4-hydroxy-3-(1H-tetrazol-5-yl)-1H-quinolin-2-one");

EP 613 618 ("4-carboxymethyl-chroman-4-carboxylic acid");

U.S. Pat. No. 5,215,570 ("N-(2-methoxy-benzoyl)-4-(3-methylureido)-benzenesulfonamide");

EP 929 543 ("3-oxo-isothiochroman-4-ylidenemethoxy)-acetic acid methyl ester").

The herbicidally active compounds from amongst groups D1 to D16 are described, for example, in "Herbizide [Herbicides]", Hock, Fedtke, Schmidt, 1st edition, Thieme 1995 (s. "quinclorac" p. 238, "molinat" p. 32, "butachlor" p. 32, "pretilachlor" p. 32, "dithiopyr" p. 32, "mefenacet" p. 32, "fenoxapropethyl" p. 216, "dimepiperate" p. 32, "pyrazolynate" p. 146, "pyrazoxyfen" p. 146, "bensulfuronmethyl" p. 31, "pyrazosulfuron-ethyl" p. 31, "cinosulfuron" p. 31, "benfuresate" p. 233, "bromobutide" p. 243, "dymron" p. 243, "dimethyametryn" p. 118, "esprocarb" p. 229, "pyributicarb" p. 32, "cinemthylin" p. 32, "propanil" p. 32, "2,4-D" p. 30, "bentazon" p. 30, "azimsulfuron (DPX-A-8947)" p. 175, "mecoprop-P" p. 237, "chlorpropham" p. 205, "ethoxyfen" p. 30, "haloxyfop-P-methyl" p. 38, "haloxyfop-ethoxyethyl" p. 38, "flumiclorac-pentyl" p. 35, "flupropacil" p. 143, "nipyraclofen" p. 145, "ethamet-sulfuron-methyl" p. 36, "thifensulfuron-methyl" p. 35, "pyrithiobac acid" p. 181);

"Agricultural Chemicals", Book II Herbicides, 1993 (s. "thiobencarb" p. 85, "benzofenap" p. 221, "napropanilid" p. 49, "piperophos" p. 102, "anilofos" p. 241, "imazosulfuron (TH-913)" p. 150, "etobenzamid (HW-52)" p. 54, "sulcotrione (ICIA-0051)" p. 268, "poast" p. 253, "focus" p. 222, "dimethenamid" p. 48, "sulfosate" p. 236, "2,4-DB" p. 10, "dichlorprop-P" p. 6, "flupoxam" p. 44, "prosulfocarb" p. 84, "quinmerac" p. 233, "metazachlor" p. 64, "flurtamone" p. 265, "bromofenoxim" p. 228, "fomesafen" p. 248, "imazamethabenz-methyl" p. 153, "clodinafop-propargyl" p. 214, "fenoxaprop-P-ethyl" p. 208, "fluazifop-P-butyl" p. 207, "quizalofop-P-ethyl" p. 210, "quizalofop-terfuryl" p. 211, "flumioxazin" p. 43, "flumipropyn" p. 267, "sulfentrazone" p. 261, "thiazopyr" p. 226, "pyrithiobac-sodium" p. 266, "amidosulfuron" p. 151, "halosulfuron-methyl" p. 148, "rimsulfuron" p. 138, "tribenuron-methyl" p. 139, "triflusul-furon-methyl" p. 137, "primisulfuron-methyl" p. 147);

"Agricultural Chemicals", Book II Herbicides, 13th Edition (s. "carfenstole" p. 284, "sulfosulfuron" p. 145, "ethoxysulfuron" p. 149, "pyribenzoxym" p. 279, "diflufenzopyr" p. 90, "ET-751" p. 278, "carfentrazone-ethyl" p. 267, "fluthiacet-methyl" p. 277, "imazapic" p. 160, "butenachlor" p. 54, "tiocarbazil" p. 84, "fluthiamide" p. 62, "isoxaflutole" p. 283, "butroxydim" p. 259)

"Short Review of Herbicides & PGRs 1991, Hodogaya Chemicals (s. "furyloxyfen" p. 142, "triazofenamid" p. 268, "thenylchlorid (NSK-850)" p. 52, "cumyluron (JC-940)" p. 90, "pendimethalin (AC-92553)" p. 58, "buthidazole" p. 88, "cyprazole" p. 38, "allidochlor" p. 48, "benzoylprop-ethyl" p. 38, "chlorthiamid" p. 150, "diphenamid" p. 34, "flamprop-methyl" p. 40, "fosamin" p. 232, "isoxaben" p. 42, "monalide" p. 32, "naptalam" p. 36, "pronamid" p. 34, "bialaphos" p. 234, "glufosinate-ammonium" p. 234, "glyphosate" p. 232, "amitrol" p. 254, "clomeprop p. 20, "dichlorprop" p. 6, "fenoprop" p. 8, "fluroxypyr" p. 156, "MCPA" p. 4, "MCPB" p. 8, "mecoprop" p. 6, "napropamide" p. 16, "triclopyr" p. 154, "chloramben" p. 28, "dicamba" p. 26, "clomazone" p. 268, "diflufenican" p. 42, "fluorochloridone" p. 266, "fluridone" p. 156, "asulam" p. 112, "barban" p. 100, "butylate" p. 106, "carbetamide" p. 36, "chlorobufam" p. 100, "cycloate" p. 108, "desmedipham" p. 104, "di-allate" p. 106, "EPTC" p. 108, "orbencarb" p. 112, "pebulate" p. 106, "phen-isopham" p. 118, "phenmedipham" p. 104, "propham" p. 100, "sulfallate" p. 110, "terbucarb" p. 102, "tri-allate" p. 108, "vemolate" p. 108, "acetochlor" p. 48, "alachlor" p. 46, "diethathyl-ethyl" p. 48, "dimethachlor" p. 50, "metolachlor" p. 46, "propachlor" p. 44, "pyrnachlor" p. 44, "terbuchlor" p. 48, "xylachlor" p. 52, "alloxydim" p. 260, "clethodim" p. 270, "cloproxydim" p. 268, "tralkoxydim" p. 270, "dalapon" p. 212, "ethofumesate" p. 124, "benefin" p. 54, "butralin" p. 58, "dinitramin" p. 56, "ethalfluralin" p. 60, "fluchloralin" p. 54, "isopropalin" p. 58, "nitralin" p. 58, "oryzalin" p. 60, "prodiamine" p. 62, "profluralin" p. 54, "trifluralin" p. 54, "dinoseb" p. 128, "dinoseb-acetate" p. 128, "dinoterb" p. 128, "DNOC" p. 126, "acifluorfen-sodium" p. 142, "aclonifen" p. 146, "bifenox" p. 140, "chlornitrofen" p. 138, "difenoxuron" p. 76, "fluorodifen" p. 138, "fluoroglycofen-ethyl" p. 146, "lactofen" p. 144, "nitrofen" p. 136, "nitrofluorfen" p. 140, "oxyfluorfen" p. 140, "cyperquat-chloride" p. 158, "difenzoquat-methyl-sulfate" p. 160, "diquat" p. 158, "paraquat-dichloride" p. 158, "benzthiazuron" p. 82, "buturon" p. 66, "chlorbromuron" p. 72, "chloroxuron" p. 76, "chlorotoluron" p. 74, "cycluron" p. 84, "dimefuron" p. 88, "diuron" p. 70, "ethidimuron" p. 86, "fenuron" p. 64, "fluometuron" p. 68, "isoproturon" p. 80, "isouron" p. 88, "karbutilate" p. 76, "linuron" p. 72, "methabenzthiazuron" p. 82, "metoxuron" p. 72, "monolinuron" p. 66, "monuron" p. 64, "neburon" p. 72, "siduron" p. 68, "tebuthiuron" p. 86, "trimeturon" p. 64, "isocarbamid" p. 168, "imazamethapyr" p. 172, "imazapyr" p. 170, "imazaquin" p. 170, "imazethapyr" p. 172, "methazole" p. 162, "oxadiazon" p. 162, "tridiphane" p. 266, "bromoxynil" p. 148, "ioxynil" p. 148, "diclofop-methyl" p. 16, "fenthiaprop-ethyl" p. 20, "fluazifop-butyl" p. 18, "haloxyfop-methyl" p. 18, "isoxapyrifop" p. 22, "propaquizafop" p. 24, "quizalofop-ethyl" p. 20, "chlorfenac" p. 258, "chlorfenprop-methyl" p. 258, "chloridazon" p. 174, "maleic hydrazide" p. 162, "norflurazon" p. 174, "pyridate" p. 176, "clopyralid" p. 154, "picloram" p. 154, "chlorimuron-ethyl" p. 92, "chlorsulfuron" p. 92, "flazasulfuron" p. 96, "metsulfuron-methyl" S.92, "nicosulfuron" p. 96, "sulfometuron-methyl" p. 92, "triasulfuron" p. 94, "ametryn" p. 198, "atrazine" p. 188, "aziprotryne" p. 206, "cyanazine" p. 192, "cyprazine" p. 192, "desmetryne" p. 200, "dipropetryn" p. 202, "eglinazine-ethyl" p. 208, "hexazinone" p. 208, "procyazine" p. 192, "prometone" p. 196, "prometryn" p. 196, "propazine" p. 188, "secbumeton" p. 196, "simazine" p. 188, "simetryn" p. 196, "terbumeton" p. 204, "terbutryn" p.

198, "terbutylazine" p. 190, "trietazine" p. 188, "ethiozine" p. 210, "metamitron" p. 206, "metribuzin" p. 202, "bromacil" p. 180, "lenacil" p. 180, "terbacil" p. 180, "benazolin" p. 262, "bensulide" p. 228, "benzofluor" p. 266, "butamifos" p. 228, "DCPA" p. 28, "dichlobenil" p. 148, "endothal" p. 264, "mefluidide" p. 306, "perfluidone" p. 260, "terbuchlor" p. 48);

"Global Herbicide Directory" First Edition, 1994 (s. "oxadiargyl" p. 96);

"European Directory of Agrochemical Products" Volume 2—Herbicides" Fourth Edition, (s. "buminafos" p. 255).

Moreover, the compound "DEH-112" is disclosed in European Patent Application EP-A 302 203. The compound "tepraloxydim" is described in DE-A 33 36 140; the compound "cinidon-ethyl" in DE-A 36 03 789, "fencarbazone" in EP 507 171, "foramsulfuron" in U.S. Pat. No. 5,922,646, "propoxycarbazone" in EP 507 171 and the compound "fluorbentranil" in EP-A 84 893. Other compounds are known from "Brighton Crop Protection Conference—Weeds—1993" (S. "thidiazimin" p. 29, "AC-322140" p. 41, "KIH-6127" p. 47, "prosulfuron" p. 53, "KIH-2023" p. 61, "metobenzuron" p. 67). The compound "carfenstrole (CH-900)" is mentioned in EP-A 332 133, and the compound N-[[[4-methoxy-6-(trifluoro-methyl)-1,3,5-triazin-2-yl]amino]-carbonyl]-2-(trifluoromethyl-benzenesulfonamide) is described in PCT/EP 96/03996.

The assignment of the active ingredients to the respective mechanisms of action is based on current knowledge. If several mechanisms of action apply to one active ingredient, this substance was only assigned to one mode of action.

The present invention also extends to herbicidal compositions which comprise a herbicidally active amount of a synergistic herbicidal mixture (comprising a compound of group A), a compound of group B), if desired, a compound of group C) and, if desired, a compound of group D) as described above), at least one liquid and/or solid carrier and, if desired, at least one surfactant.

The herbicidal compositions and synergistic herbicidal mixtures according to the invention can effect very good control of broad-leaved weeds and grass weeds in crops such as maize, cereals, rice and soya without damaging the crop plants, an effect observed especially even at low rates of application.

Taking into consideration the variety of application method in question, the herbicidal compositions and synergistic herbicidal mixtures according to the invention can additionally be employed in a further number of crop plants for eliminating undesirable plants. Examples of suitable crops are the following:

*Allium cepa, Ananas comosus, Arachis hypogaea, Asparagus officinalis, Beta vulgaris* ssp. *altissima, Beta vulgaris* ssp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spp., *Manihot esculenta, Medicago saliva, Musa* spp., *Nicotiana tabacum* (*N. rustica*), *Olea europaea, Oryza sativa, Phaseolus lunatus, Phaseolus vulgaris, Picea abies, Pinus* spp., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* und *Zea mays*.

Moreover, the herbicidal compositions and synergistic herbicidal mixtures according to the invention may also be employed for controlling harmful plants in modified crops. These modified crops are obtained by genetic engineering methods or by breeding, and—as a rule—they are distinguished by particular, advantageous properties, for example by resistance to certain crop protection agents, resistance to plant diseases or pathogens causing plant diseases such as particular insects or microorganism such as fungi, bacteria or viruses. Other particular properties relate, for example, to the harvested material in terms of quality, storing properties, composition and specific constitutions.

The mixtures according to the invention, or the herbicidal compositions comprising them, can be employed, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring.

The use forms depend on the intended purposes; in any case, they should guarantee the finest possible distribution of the active ingredients according to the invention.

Suitable inert auxiliaries are mineral oil fractions of medium to high boiling point such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, such as N-methylpyrrolidone and water.

Aqueous use forms can be prepared from emulsion concentrates, suspensions, pastes, wettable powders or waterdispersible granules by adding water. To prepare emulsions, pastes or oil dispersions, the substances, as such or dissolved in an oil or solvent, can be homogenized in water by means of wetting agent, tackifier, dispersant or emulsifier. However, it is also possible to prepare concentrates composed of active substance, wetting agent, tackifier, dispersant or emulsifier and, if appropriate, solvent or oil, and these concentrates are suitable for dilution with water.

Suitable surfactants are the alkali metal, alkaline earth metal and ammonium salts of aromatic sulfonic acids, e.g. ligno-, phenol-, naphthalene- and dibutylnaphthalene-sulfonic acid, and of fatty acids, of alkyl- and alkylaryl sulfonates, of alkyl sulfates, lauryl ether sulfates and fatty alcohol sulfates, and salts of sulfated hexa-, hepta- and octadecanols, and of fatty alcohol glycol ether, condensates of sulfonated naphthalene and its derivatives with formaldehyde, condensates of naphthalene, or of the naphthalenesulfonic acids, with phenol and formaldehyde, polyoxyethylene octylphenyl ether, ethoxylated isooctyl-, octyl- or nonylphenol, alkylphenyl and tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or concomitantly grinding the synergistic herbicidal mixture or the individual active ingredients with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic material, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The concentrations of the mixtures according to the invention in the ready-to-use products can be varied within wide ranges. In general, the formulations comprise from 0.01 to 95% by weight, preferably 0.5 to 90% by weight, of the mixture according to the invention.

The compounds of the groups A) and B), if desired, C) and, if desired D), can be formulated jointly, but also separately, and/or applied to the plants, their environment and/or seeds jointly or separately.

In case a compound of group C) is present in the mixture according to the invention it can be used for penetrating the seed of a crop plant (seed dressing), or be incorporated into the seed furrows prior to sowing. The other compounds of the groups A), B) and, if desired, D) are applied then separately from the compound of group C).

It is preferable to apply the active ingredients simultaneously. However, it is also possible to apply them separately.

Moreover, it may be advantageous to apply the herbicidal compositions and synergistic herbicidal mixtures according to the invention, jointly or separately, with additional other crop protection agents, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates can also be added.

The mixtures-according to the invention and the herbicidal compositions can be applied pre- or post-emergence. If the active ingredients are less well tolerated by certain crop plants, application techniques may be used in which the herbicidal compositions are sprayed, with the aid of the spray apparatus, in such a way that they come into as little contact, if any, with the leaves of the sensitive crop plants while reaching the leaves of undesirable plants which grow underneath, or the bare soil (post-directed, lay-by).

In the case of a post-emergence treatment of the plants, the herbicidal compositions according to the invention are preferably applied by foliar application. Application may be effected, for example, by usual spraying techniques with water as the carrier, using amounts of spray mixture of approx. 100 to 1000 l/ha. The compositions may also be applied by the so-called "low-volume" and "ultra-low-volume" methods, or in the form of so-called granules.

As a rule, the synergistic herbicidal mixtures comprise the compounds of the groups A) and B) if desired, C) and, if desired, D) in such weight ratios that the synergistic effect takes place.

The ratios of the compounds of the groups A) and B) in the mixture preferably range from 1:0.0002 to 1:50, preferably from 1:0.005 to 1:7.5, particularly preferably from 1:0.01 to 1:4.

The ratios of the compounds of the groups A) and C) in the mixture preferably range from 1:0.002 to 1:50, preferably from 1:0.02 to 1:12.5, particularly preferably from 1:0.03 to 1:6.

The ratios of the compounds of the groups A) and D) in the mixture preferably range from 1:0.001 to 1:400, preferably from 1:0.005 to 1:200, particularly preferably from 1:0.006 to 1:16.

The rate of application of pure synergistic herbicidal mixture, i.e. without formulation auxiliaries, amounts to 0.1 to 5000 g/ha, preferably 1 to 2000 g/ha, in particular 5 to 1000 g/ha, of active substance (a.s.), depending on the intended aim, the season, the target plants and growth stage.

The rate of application of picolinafen is 10 to 500 g/ha, as a rule 20 to 100 g/ha, preferably 25 to 75 g/ha, of active substance (a.s.).

The application of the compound of group B) is 0.1 to 500 g/ha, as a rule 0.5 to 150 g/ha, preferably 1 to 100 g/ha, of active substance (a.s.).

Especially the application rate of chloransulam is 1 to 100 g/ha, as a rule 5 to 75 g/ha, preferably 10 to 50 g/ha, of active substance (a.s.).

Especially the application rate of diclosulam is 1 to 500 g/ha, as a rule 10 to 100 g/ha, preferably 20 to 75 g/ha, of active substance (a.s.).

Especially the application rate of florasulam is 1 to 500 g/ha, as a rule 20 to 100 g/ha, preferably 35 to 75 g/ha, of active substance (a.s.).

Especially the application rate of flumetsulam is 10 to 300 g/ha, as a rule 30 to 150 g/ha, preferably 50 to 100 g/ha, of active substance (a.s.).

Especially the application rate of metsulam is 0.1 to 500 g/ha, as a rule 0.5 to 100 g/ha, preferably 1 to 50 g/ha, of active substance (a.s.).

Especially the application rate of penoxsulam is 0.5 to 250 g/ha, as a rule 1 to 100 g/ha, preferably 5 to 25 g/ha, of active substance (a.s.).

The preferred rate of application of the optional compound of group C) is 1 to 500 g/ha, as a rule 2 to 250 g/ha, preferably 2.5 to 100 g/ha, of active substance (a.s.).

As a rule the application rate of cloquintocet is 1 to 50 g/ha, of active substance (a.s.).

As a rule the application rate of isoxadifen is 25 to 150 g/ha, of active substance (a.s.).

As a rule the application rate of mefenpyr is 10 to 100 g/ha, of active substance (a.s.).

The preferred rate of application of the optional compound of group D) is 0.5 to 4000 g/ha, of active substance (a.s.).

As a rule the application rate of a sulfonylurea of group D) is from 0.5 to 250 g/ha, as a rule from 1 to 125 g/ha, of active substance (a.s.).

USE EXAMPLES

The mixtures according to the invention were applied pre- or post-emergence (foliar treatment). The herbicidal compounds of groups A) and B) and, if desired, C) and, if desired, D) were applied in the formulation in which they are present as commercially available product.

The herbicidally active compounds of the groups A), B) and, if desired, C) and, if desired, D) were applied in succession or jointly, in the latter case in some cases as a tank mix and in some cases as a readymix, in the form of emulsions, aqueous solutions or suspensions, the vehicle being water (300-400 l/ha). In the case of the field trials, application was effected with the aid of a mobile plot sprayer.

The test period extended over 3 to 8 weeks, and the stands were also observed at later points in time.

Damage by the herbicidal compositions was evaluated with reference to a scale of 0% to 100% in comparison with untreated control plots. 0 means no damage and 100 means complete destruction of the plants.

The following examples will demonstrate the action of the herbicidal compositions which can be used according to the invention, without excluding the possibility of other uses.

In these examples, the value E at which only an additive effect of the individual active ingredients is to be expected was calculated by the method of S. R. Colby (Calculating synergistic and antagonistic responses of herbicide combinations, Weeds 15, 20 pp (1967)).

This was done using the formula $$E = X + Y - \frac{XY}{100}$$

where
X=Percentage of the herbicidal action of the compound of group A) at an application rate of a;
Y=Percentage of the herbicidal action of the compound of group B) at an application rate of b;
E=expected herbicidal action of the compounds of the groups A)+B) at rates of application a+b (in %).

If the value observed exceeds the value E calculated in accordance with Colby's formula, then synergism is present.

The herbicidal mixtures according to the invention, like mixtures of picolinafen with florasulam or picolinafen with metosulam at appropriate application rates under post emergence conditions, exert a greater herbicidal action than would have been expected according to Colby on the basis of the observed effects of the individual components when used alone.

We claim:

1. A synergistic herbicidal mixture consisting of
A) picolinafen (I)

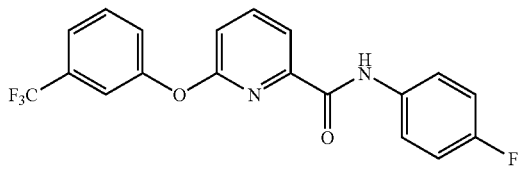

or an environmentally compatible salt thereof; and
B) a synergistically effective amount of at least one of florasulam or metosulam or an environmentally compatible salt or ester thereof;
and, if desired,
C) at least one safener selected from the group consisting of dichlormid, benoxacor, LAB 145 138, MG-191, furilazole, cyometrinil, oxabetrinil, fluxofenim, flurazole, naphthalic acid anhydride, fenclorim, fenchlorazole-ethyl, mefenpyr, isoxadifen, cloquintocet, 1-ethyl-4-hydroxy-3(1H-tetrazol-5-yl)-1H-quinolin-2-one, 4-carboxymethyl-chro-man-4-carboxylic acid, N-(2-methoxybenzyl)-4-(3-methyl-ureido)-benzenesulfonamide and (3-oxo-isothiochroman-4-ylidenmethoxy) acetic acid methyl ester; or an environmentally compatible salt, ester or amide thereof.

2. A synergistic herbicidal mixture as claimed in claim 1 comprising, as a component C) cloquintocet.

3. A synergistic herbicidal mixture as claimed in claim 1, further comprising as component D) at least one of an acetyl-CoA carboxylase inhibitor (ACC), amide, auxin herbicide, auxin transport inhibitor, carotenoid biosynthesis inhibitor, enolpyruvylshikimate 3-phosphate synthase inhibitor (EPSPS), glutamine synthetase inhibitor, lipid biosynthesis inhibitor, mitosis inhibitor, protoporphyrinogen IX oxidase inhibitor, photosynthesis inhibitor, synergist, growth substance, or cell wall biosynthesis inhibitor.

4. A synergistic herbicidal mixture as claimed in claim 1 comprising as active ingredients only picolinafen and one compound of group B).

5. A synergistic herbicidal mixture as claimed in claim 1 comprising as active ingredients only picolinafen, one compound of group B) and one compound of group C).

6. A synergistic herbicidal mixture as claimed in claim 1 comprising as active ingredients only picolinafen, one compound of group B) and one compound of group D).

7. A synergistic herbicidal mixture as claimed in claim 1 comprising as active ingredients only picolinafen, one compound of group B), one compound of group C) and one compound of group D).

8. A synergistic herbicidal mixture as claimed in claim 1 wherein the ratios by weight of the compounds of the groups A) and B) range from 1:0.0002 to 1:7.5.

9. A synergistic herbicidal mixture as claimed in claim 1 wherein the ratios by weight of the compounds of the groups A) and C) range from 1:0.002 to 1:12.5.

10. A synergistic herbicidal mixture as claimed in claim 3 wherein the ratios by weight of the compounds of the groups A) and D) range from 1:0.001 to 1:200.

11. A herbicidal composition comprising a herbicidally active amount of a synergistic herbicidal mixture as claimed in claim 1 further comprising, at least one liquid and/or solid carrier and, if desired, at least one surfactant.

12. A process for the preparation of a herbicidal composition as claimed in claim 11, comprising mixing the compounds of group A), B), if desired, C), if desired, D), at least one liquid and/or solid carrier and, if desired, at least one surfactant.

13. A method for controlling undesired vegetation, which comprises applying to undesired plants a synergistic herbicidal mixture as claimed in claim 1, during and/or after the emergence of the undesired plants, it being possible for the active compounds of the groups A), B), if desired, C) and, if desired D) to be applied simultaneously or in succession.

14. A method for controlling undesired vegetation comprising simultaneously or successively applying to undesired plants, their habitation or their seeds an herbicidal combination consisting of
A) picolinafen (I)

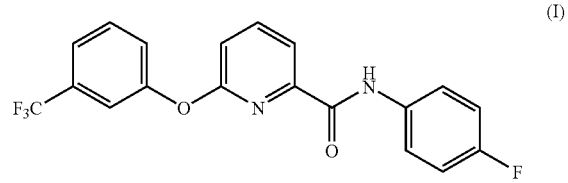

or an environmentally compatible salt thereof; and
B) a synergistically effective amount of at least one of florasulam or metosulam or an environmentally compatible salt or ester thereof; and, if desired, C) at least one safener selected from the group consisting of dichlormid, benoxacor, LAB 145 138, MG-191, furilazole, cyometrinil, oxabetrinil, fluxofenim, flurazole, naphthalic acid anhydride, fenclorim, fenchlorazole-ethyl, mefenpyr, isoxadifen, cloquintocet, 1-ethyl-4-hydroxy-3(1H-tetrazol-5-yl)-1H-quinolin-2-one, 4-carboxymethyl-chro-man-4-carboxylic acid, N-(2-methoxybenzyl)-4-(3-methyl-ureido)-benzenesulfonamide and (3-oxo-isothiochroman-4-ylidenmethoxy) acetic acid methyl ester;

or an environmentally compatible salt, ester or amide thereof.

* * * * *